(12) United States Patent
Flanagan et al.

(10) Patent No.: US 11,975,158 B2
(45) Date of Patent: May 7, 2024

(54) MEDICAL DEVICE WITH HAPTIC SENSING CAPABILITIES

(71) Applicant: BOSTON SCIENTIFIC SCIMED, INC., Maple Grove, MN (US)

(72) Inventors: Aiden Flanagan, Kilcolgan (IE); Finn Matthews, Kilcolgan (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 527 days.

(21) Appl. No.: 17/129,198

(22) Filed: Dec. 21, 2020

(65) Prior Publication Data
US 2021/0213249 A1    Jul. 15, 2021

Related U.S. Application Data

(60) Provisional application No. 62/959,658, filed on Jan. 10, 2020.

(51) Int. Cl.
*A61M 25/00*    (2006.01)
*A61M 25/01*    (2006.01)

(52) U.S. Cl.
CPC .... *A61M 25/0082* (2013.01); *A61M 25/0133* (2013.01); *A61M 2025/0002* (2013.01); *A61M 2025/0096* (2013.01); *A61M 2205/3592* (2013.01)

(58) Field of Classification Search
CPC ...... A61M 25/0133; A61M 2025/0002; A61B 5/0215; A61B 5/02158; A61B 2090/065
See application file for complete search history.

(56) References Cited

U.S. PATENT DOCUMENTS

| 5,438,873 | A | 8/1995 | Wlodarczyk et al. |
| 5,873,835 | A | 2/1999 | Hastings et al. |
| 5,993,378 | A | 11/1999 | Lemelson et al. |
| 6,264,612 | B1 * | 7/2001 | McConnell ............ A61B 5/036 600/561 |
| 6,659,959 | B2 | 12/2003 | Brockway et al. |
| 7,749,215 | B1 * | 7/2010 | Ben-Haim ........ A61M 25/0084 604/510 |

(Continued)

FOREIGN PATENT DOCUMENTS

WO    WO-0247751 A2 *  6/2002  ........... A61B 5/0215

OTHER PUBLICATIONS

Intentional Search Report and Written Opinion dated Mar. 23, 2021 for International Application No. PCT/US2020/066429.

(Continued)

*Primary Examiner* — Laura A Bouchelle
(74) *Attorney, Agent, or Firm* — Seager, Tufte & Wickhem, LLP

(57) ABSTRACT

Medical devices and methods for using medical devices are disclosed. An example medical device includes a catheter having a proximal end region and a distal tip and an array of sealed chambers disposed along the distal tip, wherein each of the chambers includes a distal membrane disposed along an outer surface of the distal tip and a proximal membrane extending radially inward from the outer surface. Further, each proximal membrane is configured to shift between a first position and an expanded position in response to a change in pressure within the chamber.

15 Claims, 10 Drawing Sheets

(56) References Cited

U.S. PATENT DOCUMENTS

| | | | |
|---|---|---|---|
| 8,858,451 B2* | 10/2014 | Pfeiffer | A61M 25/0097 600/485 |
| 9,669,144 B2* | 6/2017 | Spanier | A61M 25/01 |
| 9,770,225 B2 | 9/2017 | Ahmed et al. | |
| 10,117,620 B2 | 11/2018 | Gustafsson | |
| 10,154,787 B2 | 12/2018 | Belleville | |
| 2007/0282211 A1 | 12/2007 | Ofek et al. | |
| 2009/0326390 A1 | 12/2009 | Belalcazar et al. | |
| 2013/0274712 A1 | 10/2013 | Schecter et al. | |

OTHER PUBLICATIONS

International Search Report and Written Opinion, International Application No. PCT/US2020/066429, dated Mar. 23, 2021 (42 pgs).

\* cited by examiner

MEDICAL DEVICE WITH HAPTIC SENSING CAPABILITIES

CROSS REFERENCE TO RELATED APPLICATIONS

The present application claims the benefit of and priority to U.S. Provisional Patent Application Ser. No. 62/959,658, filed on Jan. 10, 2020, the disclosure of which is incorporated herein by reference.

TECHNICAL FIELD

The present disclosure pertains to medical devices, and methods for manufacturing medical devices. More particularly, the present disclosure pertains to a medical device with haptic sensing capabilities.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a catheter having a proximal end region and a distal tip and an array of sealed chambers disposed along the distal tip, wherein each of the chambers includes a distal membrane disposed along an outer surface of the distal tip and a proximal membrane extending radially inward from the outer surface. Further, each proximal membrane is configured to shift between a first position and an expanded position in response to a change in pressure within the chamber.

Alternatively or additionally to any of the embodiments above, further comprising a plurality of fibers, wherein each fiber has a proximal end and a distal end, wherein the distal end of each fiber is coupled to a pressure sensor aligned with a single proximal membrane, and wherein each pressure sensor is coupled to its corresponding proximal membrane.

Alternatively or additionally to any of the embodiments above, wherein each sensor is configured to measure the extent to which proximal membrane shifts between the first position and the expanded position.

Alternatively or additionally to any of the embodiments above, wherein each of the array of sealed chambers is filled with an incompressible fluid.

Alternatively or additionally to any of the embodiments above, wherein each of the array of sealed chambers is filled with an emulsion.

Alternatively or additionally to any of the embodiments above, wherein the emulsion includes a plurality of light reflective particles disposed within an incompressible fluid.

Alternatively or additionally to any of the embodiments above, wherein the extent to which each of the proximal membranes expands directly corresponds to the extent of pressure change within the respective chamber to which the membrane is connected.

Alternatively or additionally to any of the embodiments above, wherein each of the proximal membranes shifts from the first position to the expanded positioned in response to a deflection of its corresponding distal membrane.

Alternatively or additionally to any of the embodiments above, wherein each pressure sensor is designed to transmit a pressure signal along its corresponding fiber, and wherein the pressure signal corresponds to the pressure change in the chamber to which the sensor corresponds.

Alternatively or additionally to any of the embodiments above, wherein each of the sealed chambers includes a first cavity in fluid communication with a second cavity, wherein the first cavity includes a first diameter and wherein the second cavity includes a second diameter different from the first diameter.

Alternatively or additionally to any of the embodiments above, wherein each of the fibers of the plurality of fibers includes an optical fiber.

Alternatively or additionally to any of the embodiments above, wherein the distal end of each of the plurality of optical fibers is spaced away from the proximal membrane, and wherein each of the plurality of optical fibers is configured to transmit a first light signal onto the proximal membrane.

Alternatively or additionally to any of the embodiments above, wherein each of the first light signals transmitted onto its corresponding proximal membrane is reflected back to each respective optical fiber, and wherein the reflected light signals correspond to the shifting of each of the respective proximal membranes.

Alternatively or additionally to any of the embodiments above, wherein comparing the first light signal with the reflected light signal directly corresponds to a change in pressure of the chamber.

Another example medical device system includes a processor, a catheter having a proximal end region and a distal tip, the proximal end region coupled to the processor and a plurality of fluid sealed chambers disposed along the distal tip, wherein each of the chambers includes a distal membrane disposed along an outer surface of the distal tip and a proximal membrane extending radially inward from the outer surface. The medical device also includes a plurality of fibers, wherein each fiber has a proximal end and a distal end, wherein each distal end is aligned with a discrete proximal membrane and wherein each proximal membrane is configured to shift between a first position and an expanded position in response to a change in pressure within the chamber.

Alternatively or additionally to any of the embodiments above, further comprising a plurality of pressure sensors, wherein each pressure sensor couples a single fiber to a single proximal membrane.

Alternatively or additionally to any of the embodiments above, wherein each sensor is configured to measure the extent to which proximal membrane shifts between the first position and the expanded position, and wherein the sensor converts the extent to which each proximal membrane shifts between the first position and the expanded position corresponds into a pressure signal.

Alternatively or additionally to any of the embodiments above, wherein each sensor is designed to transmit the pressure signal to the processor.

Alternatively or additionally to any of the embodiments above, wherein the processor is configured to output an array of pressure signals corresponding to the change in pressure of each of the chambers.

An example method for measuring pressure within a body cavity includes advancing a pressure catheter to a tissue site within the body cavity, wherein the pressure catheter includes a catheter having a proximal end region and a distal tip, an array of sealed chambers disposed along the distal tip, wherein each of the chambers includes a distal membrane disposed along an outer surface of the distal tip and a proximal membrane extending radially inward from the outer surface. The pressure catheter also includes a plurality of fibers, wherein each fiber has a proximal end and a distal end, wherein each of the distal ends is aligned with a discrete proximal membrane. The method also includes engaging one or more of the distal membranes with the tissue site, deflecting one or more proximal membranes in response to the engagement of the distal membrane with the tissue site, measuring the deflection of the one or more proximal membranes, wherein the deflection of each of the one or more proximal membranes corresponds to the change in pressure within its respective chamber.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
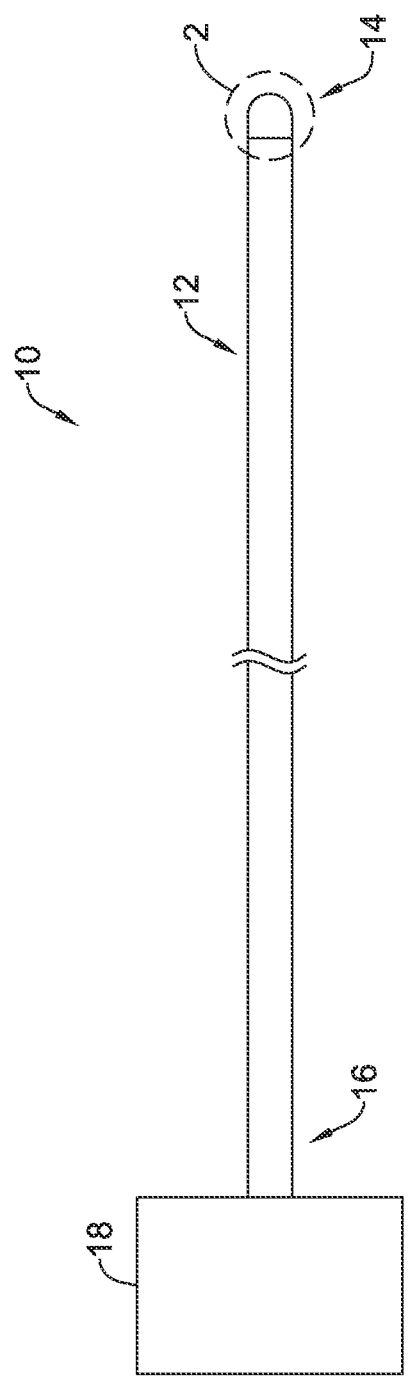
FIG. 1 is a side view of an example medical device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, including minimally invasive surgery, intravascular procedures, procedures along the digestive and/or biliary tract, ureteral procedures, etc. utilize medical devices such as catheters and guidewires. In some instances, these procedures may require clinicians to utilize medical devices than include more refined and controllable motion. Use of these medical devices may improve patient outcomes and reduce trauma and/or harm to the patient. For example, designing medical devices to include refined and controllable motion may allow easier cannulation of the bile duct during endoscopic retrograde cholangiopancreatography (ERCP). Additionally, utilizing medical devices with refined controllable motion may permit more accurate and controlled deployment of mitral and/or other heart repair devices, for example.

It can be appreciated that minimally invasive surgery is increasingly being performed with longer catheters, whereby the entry point into the body is located relatively far away from the surgery location. It can be appreciated that longer length catheters may create significant limitations on the control and/or accuracy of the procedure to be performed. Further, in some procedures, live visualization may be relatively poor and other diagnostic techniques (e.g., ultrasonic imaging, visual imaging, fluoroscopy, etc.) may give reasonable, but limited feedback to the clinician. Therefore, there is an ongoing need to design medical devices which provide real-time, accurate feedback regarding the position, force-sensing, etc. of the distal end of the medical device while the clinician is utilizing the medical device during a medical procedure. It may be desirable to design medical devices to include haptic feedback mechanisms. For example, it may be desirable to design medical devices to include micro-fluidic arrays to sense forces at the distal end of a variety of medical devices. Accordingly, example medical devices utilizing micro-fluidic arrays to incorporate haptic feedback response are disclosed.

FIG. 1 is a side view of an example medical device system 10. The medical device system 10 may include a catheter shaft 12. The catheter shaft 12 may include a distal end region 14 and a proximal end region 16. The catheter 12 may be designed to be relatively thin such that it can be manufactured to have a relatively small outer diameter and be suitable for less invasive medical procedures. For example, the catheter 12 (and/or all the catheter examples disclosed herein) may have an outer diameter of about 0.25 mm to about 20 mm, 0.5 mm to about 18 mm, 1.0 mm to about 15 mm, 2.5 to about 12 mm, or 5.0 mm to about 10 mm.

FIG. 1 further illustrates that the proximal end region 16 of the catheter 12 may be coupled to a controller 18 (e.g., processor). As will be discussed in greater detail below, the controller 18 may include one or more sensors, processors and/or signal generating elements which may communicate with the distal end region 14 of the catheter 12. Further, it can be appreciated that while a portion of the catheter 12 is positioned inside a patient's body, the controller 18 may be positioned outside the patient's body.

As discussed above, the catheter 12 may be utilized to measure forces and/or pressures at one or several intermediate sites along the catheter 12 when inserted into a closed body cavity. For example, the catheter 12 may be utilized to measure forces while performing cannulation and sensing (determining) the location of the bile and pancreatic ducts. Additionally, the catheter 12 may be utilized to locate the correct target sites in the left ventricle of the heart, the mitral leaflets and/or mitral annulus and/or the target septal crossing location in the atrial septum. Further, the catheter 12 may be utilized to diagnose abnormal tissue or the location of tumors. These are just examples. Using the catheter 12 to perform a variety of medical procedures is contemplated.

Further, while FIG. 1 has been described as including the catheter 12 coupled to the controller 18, it can be appreciated that the medical device 10 may include a guidewire or other similar devices coupled to the controller 18. For example, the medical device 10 may include an electrophysiology catheter. However, this is not intended to be limiting. Rather, it is contemplated that the medical device 10 may include a balloon catheter, stent deployment catheter, sphincterotome, cannulation catheter, ablation catheter, TAVI device, or the like.

Figure 2:
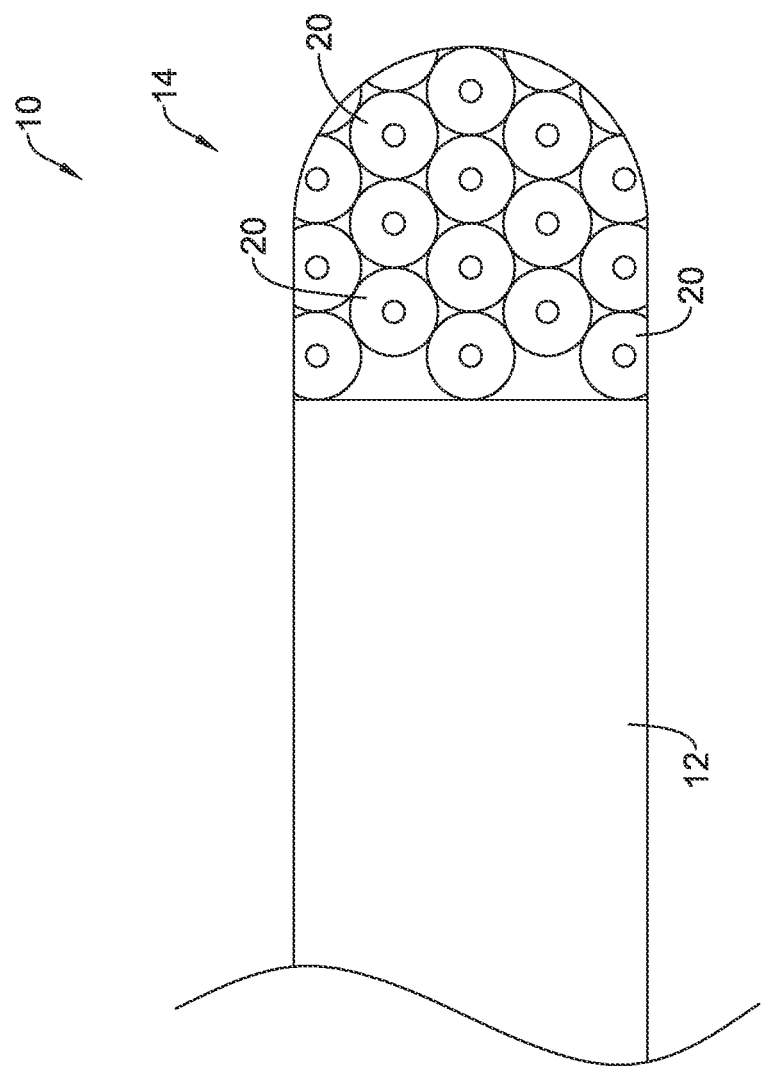
FIG. 2 is a side view of a portion of the example medical device shown in FIG. 1.

FIG. 2 illustrates a detailed view 2 of the distal end region 14 shown in FIG. 1. In particular, FIG. 2 illustrates the distal end (e.g., the distal tip) of the catheter 12. It can be appreciated that the distal tip of the distal end region 14 may be rounded. Further, as discussed above, it can be appreciated that the distal end region 14 of the catheter 12 may include one or more elements and/or features which are designed to sense and/or measure pressure and/or forces that the distal tip experiences when engaging one or more target sites in the body. For example, FIG. 2 illustrates that the distal end region 14 of the catheter 12 may include a plurality of micro-fluidic cells 20 arranged around the distal tip of the catheter 12. As will be discussed in greater detail below, each of the micro-fluidic cells 20 may be able to deform in response to engagement with a tissue structure in the body. Further, the deformation of an individual micro-fluidic cell 20 may be translated into a pressure signal which may be sensed and processed by the controller 18.

FIG. 2 illustrates that the shape of the outer surface of each of the micro-fluidic cells 20 may be substantially circular. However, this is not intended to be limiting. Rather, it is contemplated that the shape of the outer surface of the micro-fluidic cells may be square, triangular, rectangular, ovular, polygonal, combinations thereof or any other suitable geometric shape.

Figure 3:
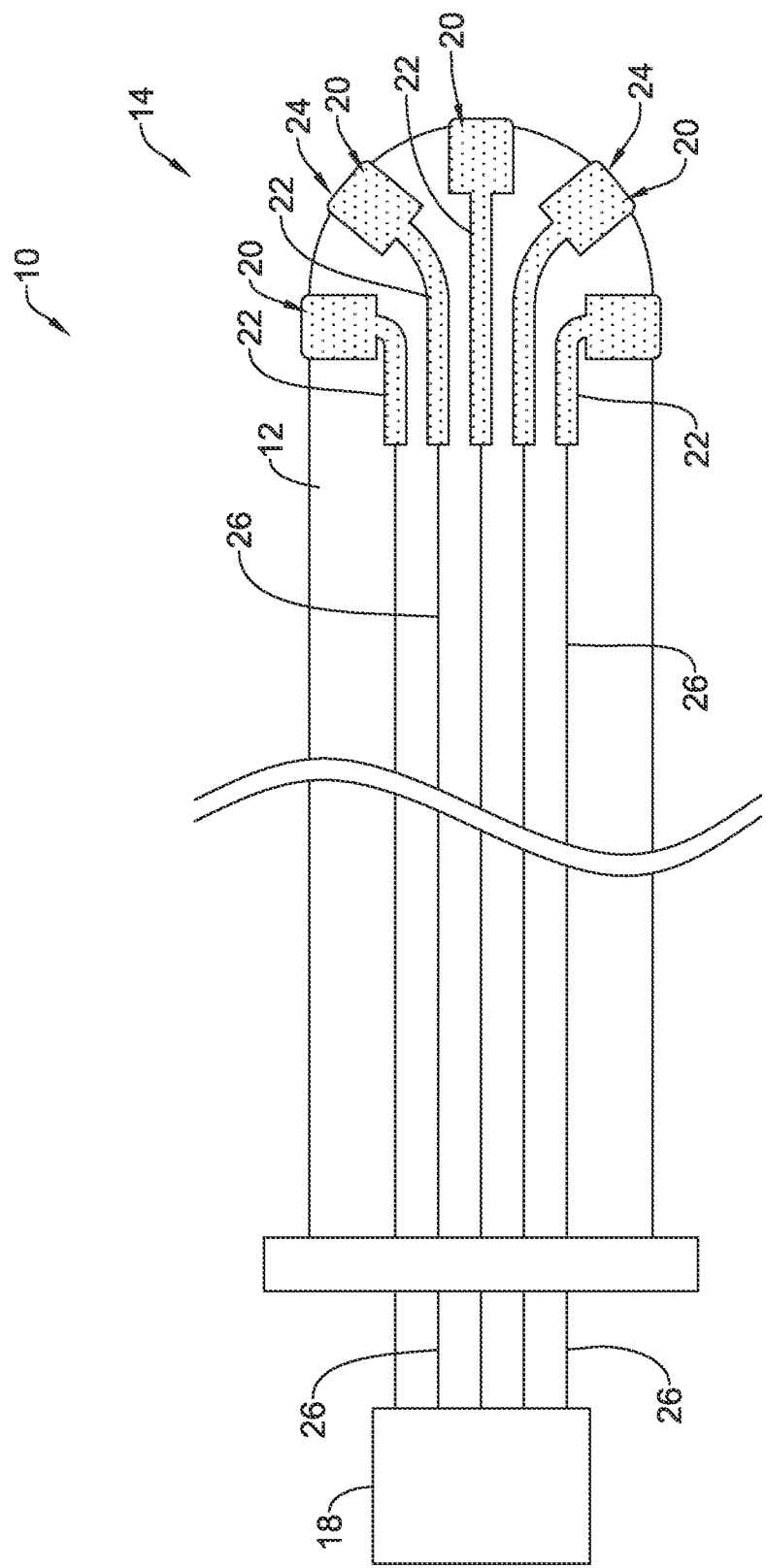
FIG. 3 is a partial cross-sectional view of an example medical device.

FIG. 3 illustrates a partial cross-section of the medical device 10 described above. In particular, FIG. 3 illustrates a partial cross-section of the distal end region 14 of the catheter 12 described above. For example, FIG. 3 illustrates a plurality of micro-fluidic cells 20 disposed along the distal tip of the distal end region 14 of the catheter 12. It can be appreciated from FIG. 3 that each of the micro-fluidic cells 20 may extend radially inward toward a central longitudinal axis of the catheter 12. In some instances, the micro-fluidic cells 20, collectively, may be referred to as a micro-fluidic array of cells 20.

As a general description, FIG. 3 illustrates that each of the micro-fluidic cells 20 may include a distal membrane 24 which extends along the outer surface of the distal end of the catheter 12. Additionally, FIG. 3 illustrates that each of the micro-fluidic cells 20 may include a fluid lumen 22. Further, the proximal end of each of the fluid lumens 22 may be coupled to a fiber 26. The fiber 26 may include a sensor (not shown in FIG. 3, but shown in FIG. 4). Each of the fibers 26 may extend through an inner lumen of the catheter 12 whereby they may terminate at the controller 18. As will be described in greater detail below, a change in force occurring along the distal membrane 24 may be transmitted through the micro-fluidic cell 20 across a sensor and finally transmitted along the fiber to the controller 18.

Figure 4:
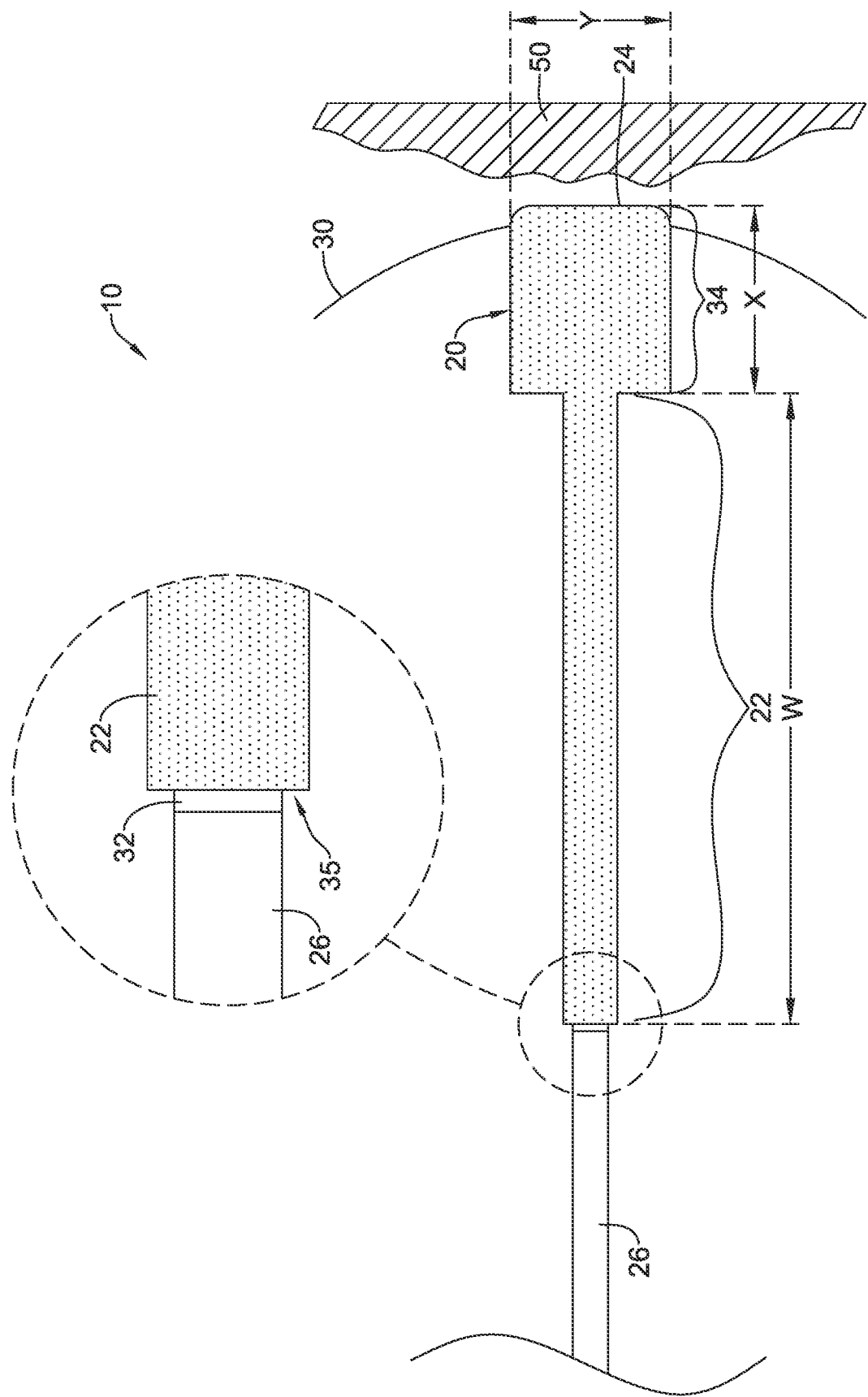
FIG. 4 is another partial cross-sectional view of an example medical device.

FIG. 4 illustrates a close-up view of a single micro-fluidic cell 20. FIG. 4 illustrates that the micro-fluidic cell 20 may include a distal membrane 24 extending along the outer surface 30 of the distal end region 14 of the catheter 12. It can be appreciated that, in some examples, the distal membrane 24 of the micro-fluidic cell 20 may be substantially flush with the outer surface 30 of the distal end region 14 of the catheter. However, in other examples, it can be appreciated that the distal membrane 24 may extend radially outward of the outer surface 30 of the distal end region 14 of the catheter.

FIG. 4 further illustrates that each micro-fluidic cell 20 may include a fluid chamber 34 which extends radially inward from the outer surface 30 of the distal end region 14 of the catheter. In some examples, the fluid chamber 34 may have a depth "X" of about 0.050 mm to 1.5 mm, or about 0.075 mm to about 1.0 mm, or about 0.100 mm to about 0.750 mm, or about 0.250 mm to about 0.500 mm. Additionally, in some examples, the fluid chamber 34 may have a width "Y" of about 0.090 mm to about 0.210 mm, or about 0.120 mm to about 0.180 mm, or about 0.140 mm to about 0.160 mm.

As discussed above, the fluid chamber 34 may transition into a fluid lumen 22. The fluid lumen 22 may continue to extend radially inward of the outer surface 30 of the distal end region 14 of the catheter 12. In other words, the fluid chamber 34 and the fluid lumen 22 may be substantially aligned, both of which extend radially inward from the outer surface 30 of the distal end region of the catheter 12. In some examples, the fluid lumen 22 may have a depth "W" of about 0.070 mm to 0.130 mm, or about 0.080 mm to 0.120 mm, or about 0.090 mm to 0.110 mm, or about 0.100 mm. Additionally, in some examples it is contemplated that the depth "W" of the fluid lumen 22 may be much longer than the aforementioned dimensional ranges. For example, it is contemplated that the fluid lumen 22 may extend along any length of the catheter, including extending the entire length of the catheter.

Additionally, FIG. 4 illustrates that each of the fluid chamber 34 and the fluid lumen 22 may be filled with a fluid (e.g., an incompressible fluid) and/or a gas. For the example shown in FIG. 4, the incompressible fluid within the fluid chamber 34 and the fluid lumen 22 is depicted by a dotted pattern in FIG. 4. However, in some examples, it can be appreciated that the dotted pattern shown in FIG. 4 may include a gas.

The detailed view of FIG. 4 further illustrates that the proximal end of the fluid chamber 34 may include a proximal membrane 35 which may be coupled to a sensor 32. The sensor 32 may be a pressure sensor 32 which is designed to sense a change in pressure of the fluid contained with the fluid chamber 34 and fluid lumen 22.

FIG. 4 further illustrates that the pressure sensor 32 may be coupled to a fiber 26. In some instances, the pressure sensor 32 may be positioned between a distal end of the fiber 26 and the proximal membrane 35 of the fluid lumen 22. Accordingly, it can be appreciated that because the sensor 32 may be coupled directly to the proximal membrane 35, it may be configured to sense changes in the proximal membrane 35. Further, the sensor 32 may be able to not only sense changes in the proximal membrane 35, but it may also be designed to translate the changes in the proximal membrane 35 into a signal which may be transmitted via the fiber 26 to the controller 18.

Figure 5:
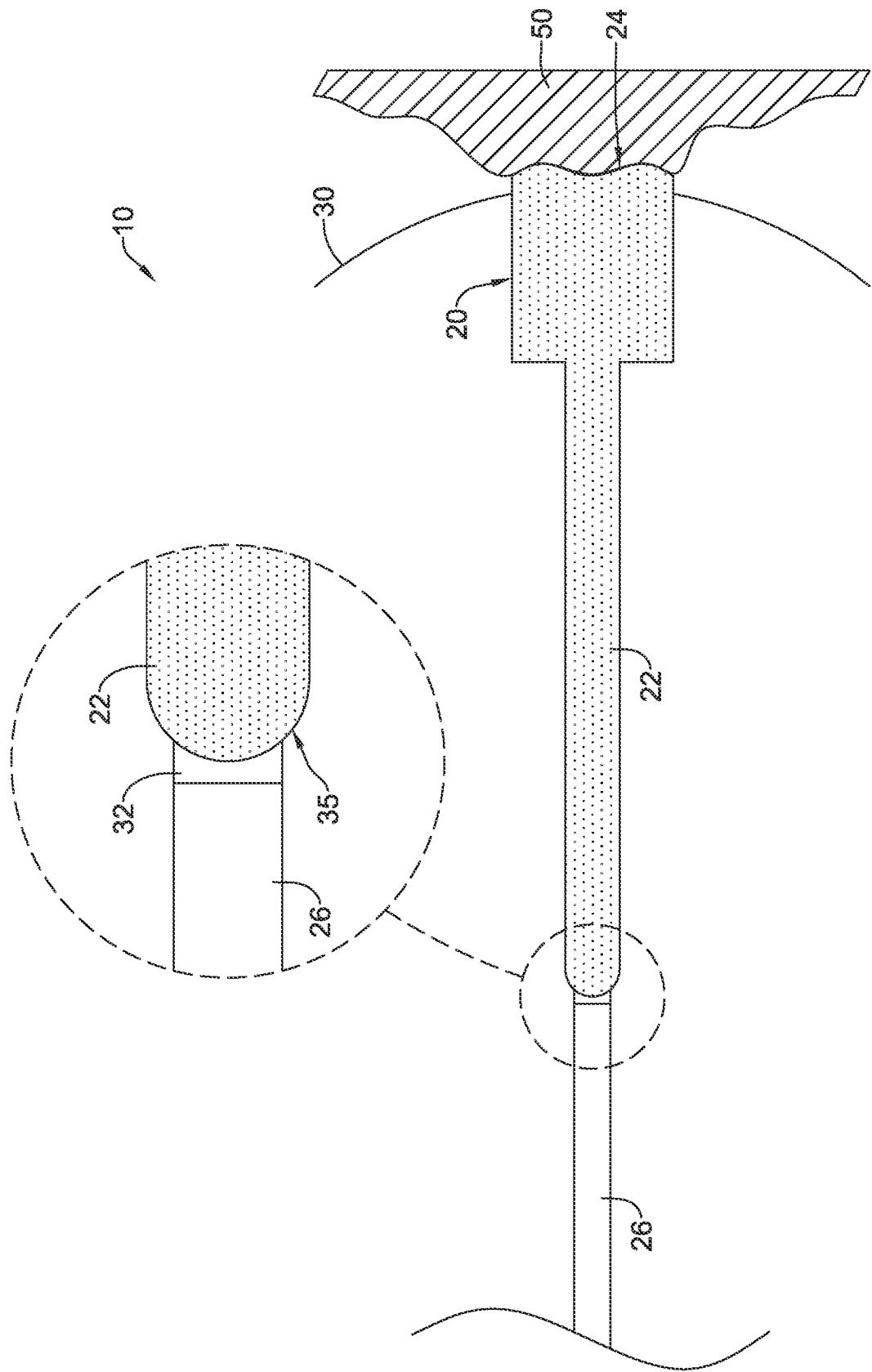
FIG. 5 is another partial cross-sectional view of an example medical device.

FIG. 4 and FIG. 5, collectively, illustrate an example in which the medical device 10 measures the pressure and/or force applied to the distal membrane 24 of the medical device 10 as the device contacts an example tissue site in the body. For example, FIG. 4 illustrates the distal membrane 24 (located along the outer surface 30 of the medical device 10, as described above) near an example tissue site 50 in a patient's body. It can be appreciated from the detailed view in FIG. 4 that the proximal membrane 35 of the fluid lumen has not deformed because the distal membrane 24 has not yet contacted the tissue site 50.

FIG. 5 illustrates the position of the medical device 10 after the medical device 10 has been advanced such that the distal membrane 24 contacts the tissue site 50. It can be appreciated from FIG. 4 and FIG. 5 that as the distal membrane 24 contacts the tissue site 50, the distal membrane 24 may deform (e.g., the distal membrane 24 may deform as it engages the contours of the tissue site 50). Further, because the micro-fluidic cell 20 and the fluid lumen 22 are filled with an incompressible fluid, changes in shape of the distal membrane 24 may cause the proximal membrane 35 to change shape. For example, the detail view of FIG. 5 illustrates the proximal membrane 35 changing shape (e.g., expanding outward, bulging proximally), as compared to FIG. 4, in response to changes in the distal membrane 24.

Further, as described above, changes in the shape of the proximal membrane 35 may be sensed by the pressure sensor 32 which may be disposed along the proximal membrane 35. Moreover, it can be appreciated that the sensor 32 may be able to sense varying degrees of deformity of the proximal membrane 35. In other words, as a clinician advances the medical device 10 distally, thereby imparting increasing force to the distal membrane 24, the proximal membrane 35 may increasingly deflect in response to the deflection of the distal membrane 24. These increased forces may be sensed (e.g., measured) by the sensor 32. Additionally, the sensor 32 may translate the physical changes in the proximal membrane 35 into force signals which may be transmitted over the fiber 26 to the controller 18.

In some examples, the proximal membrane 35 (and other proximal membranes described herein) may be a thin elastic membrane. The proximal membrane may be constructed of silicone or Chronoflex®, for example.

While FIG. 4 and FIG. 5 illustrate an example in which sensed forces are transmitted along the fiber 26 to the controller 18, it is further contemplated that, in another example, the fluid lumen 22 may extend the entire length of the catheter 12 whereby the proximal membrane 35 may be located outside the catheter 12 such that a clinician may touch the proximal membrane 35 with his or her fingertip. It can be appreciated that this design configuration may provide direct tactile feedback to the clinician about the tissue structures the distal membrane 24 is contacting via feeling the change in shape of the proximal membrane 35. In other words, in this example, a clinician may place his or her fingertip on the proximal membrane 35 (located outside the catheter 12) to feel changes in the distal membrane 24 (via force transmission through the fluid lumen 22 extending the entire length of the catheter 12).

While FIG. 4 and FIG. 5 illustrate the above pressure measurements taken by a single micro-fluidic cell 20, it can be appreciated that each individual micro-fluidic cell 20 may sense its own force measurement, thereby permitting the entire array of micro-fluidic cells 20 to transmit an array of pressure measurements to the controller 18. The controller 18 may be capable of processing the collection of pressure measurements taken from the micro-fluidic array and "map" the pressure distribution along the entire outer surface 30 of the distal end of the catheter 12.

Figure 6:
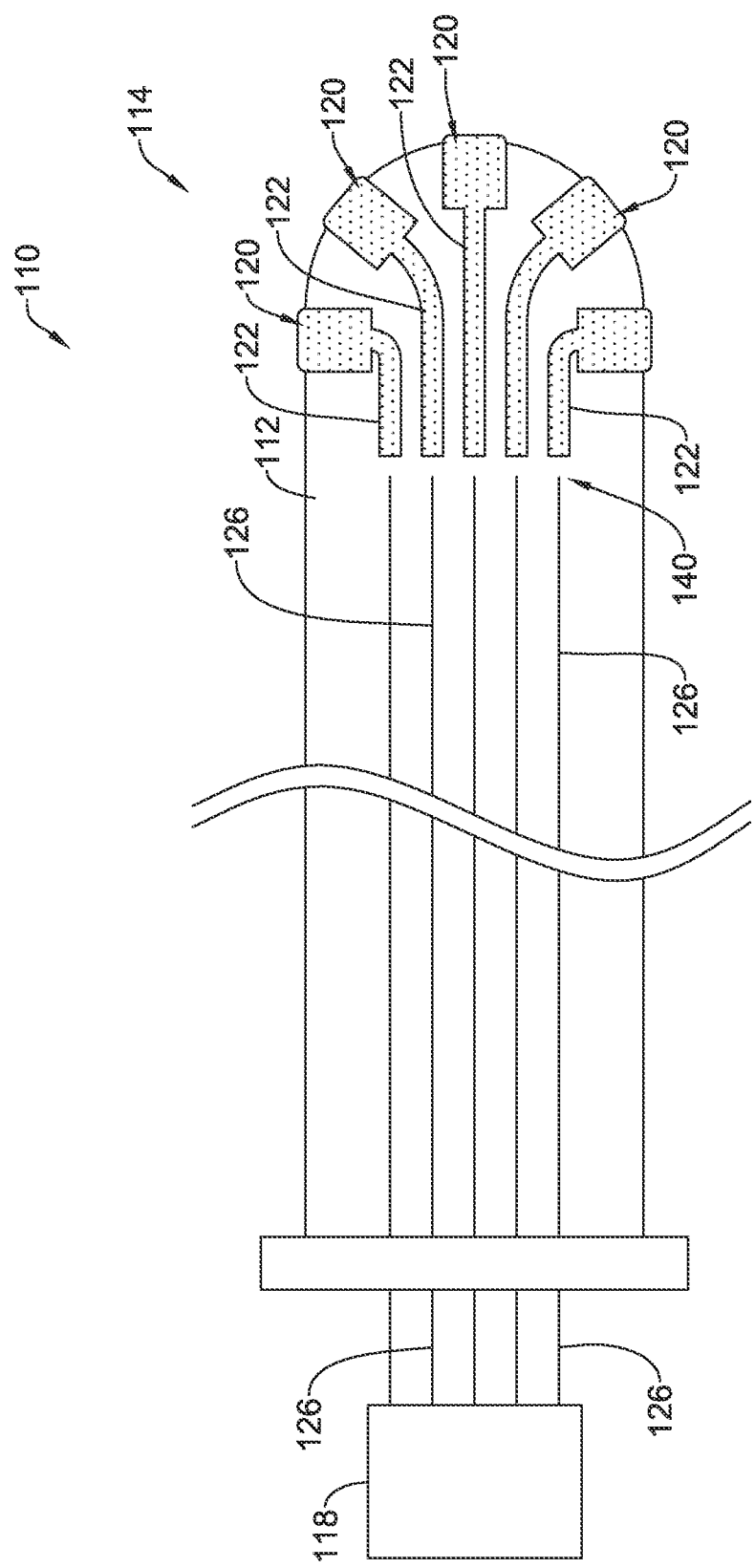
FIG. 6 is another partial cross-sectional view of an example medical device.

FIG. 6 illustrates another example medical device 110. The medical device 110 may be similar in form and function to the medical device 10 described above. For example, as shown in FIG. 6, the distal end region 114 of the catheter 112 may include a plurality of micro-fluidic cells 120 (the micro-fluidic cells 120 may be similar in form and function to the fluidic cells 20 described above), each of which transition to a fluid lumen 122 (the fluid lumens 122 may be similar in form and function to the fluid lumens 22 described above). As described above with respect the medical device 10, both micro-fluidic cell 120 and the fluid lumen 122 may be filled with an incompressible fluid. Additionally, as described above with respect the medical device 10, the micro-fluidic cell 20 may include a proximal membrane 124 (not shown in FIG. 6, but shown in FIG. 7) and the fluid lumen 122 may include a proximal membrane 135 (not shown in FIG. 6, but shown in FIG. 7).

Additionally, FIG. 6 illustrates that the medical device 110 may include a plurality of fiber optics 126 extending within the catheter 112 (e.g., extending within a lumen of the catheter 112). FIG. 6 further illustrates that the distal ends 140 of each of the fiber optics 126 may be spaced away from and aligned with a discrete fluid lumen 122. Additionally, each of the fiber optics 126 may extend proximally within the catheter 112, whereby the proximal end 140 of each of the fiber optics 126 may be coupled to a controller 118 (the controller 118 may be similar in form and function to the controller 18 described above).

As described above with respect to the medical device 10, it can be appreciated that while a portion of the catheter 112 is positioned inside a patient's body, the controller 118 may be positioned outside the patient's body.

Figure 7:
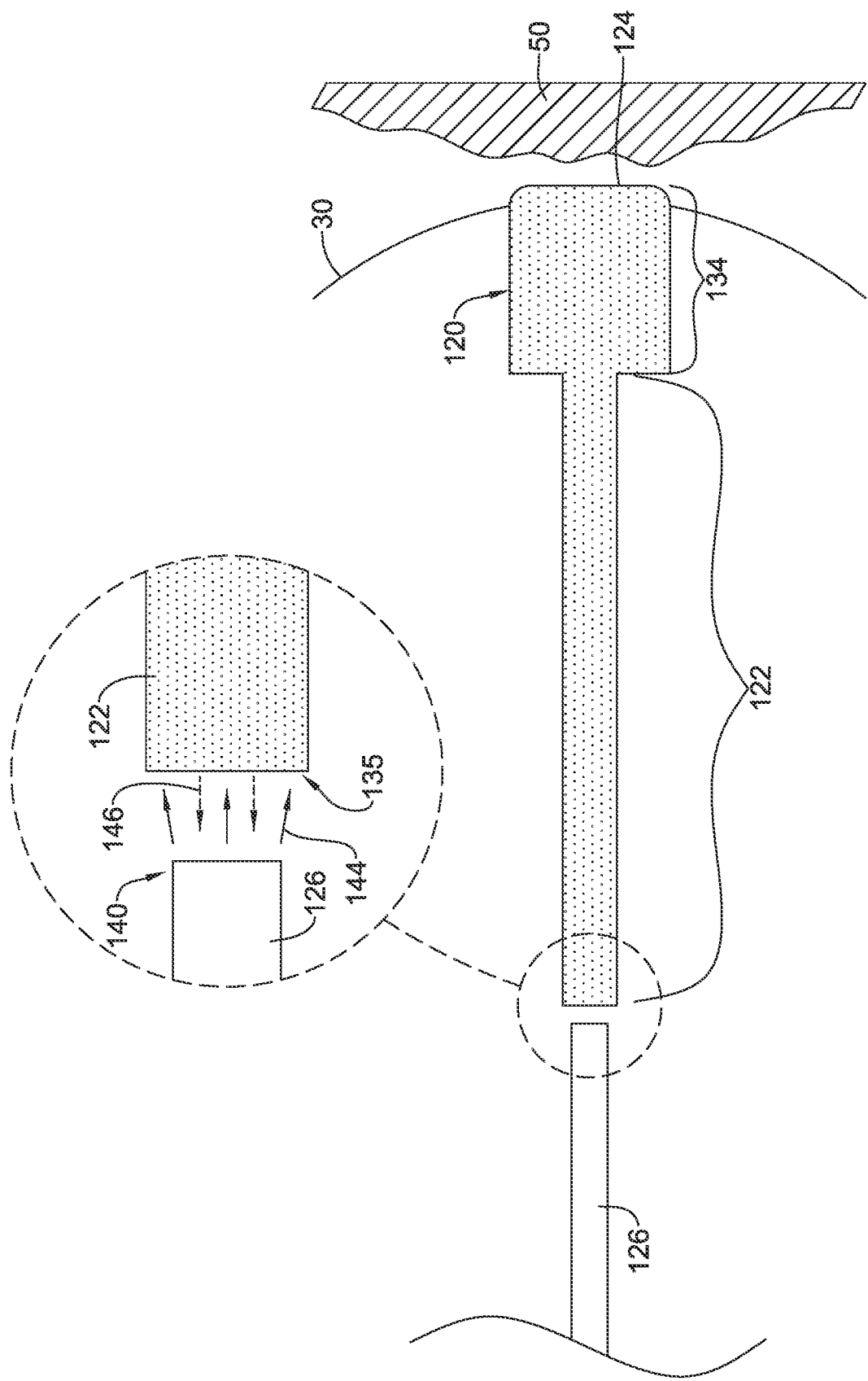
FIG. 7 is another partial cross-sectional view of an example medical device.

FIG. 7 illustrates a close-up view of a single micro-fluidic cell 120 described above. For example, FIG. 7 illustrates that the micro-fluidic cell 120 may include a distal membrane 124 extending along the outer surface 30 of the distal end region 114 of the catheter 112. It can be appreciated that, in some examples, the distal membrane 124 of the micro-fluidic cell 120 may be substantially flush with the outer surface 30 of the distal end region 14 of the catheter. However, in other examples, it can be appreciated that the distal membrane 124 may extend radially outward of the outer surface 30 of the distal end region 14 of the catheter.

FIG. 7 further illustrates that each micro-fluidic cell 120 may include a fluid chamber 134 which extends radially inward from the outer surface 30 of the distal end region 114 of the catheter. Additionally, the proximal end region of the fluid chamber 134 may transition into a fluid lumen 122. The fluid lumen 122 may continue to extend radially inward of the outer surface 30 of the distal end region 114 of the catheter 112. In other words, the fluid chamber 134 and the fluid lumen 122 may be substantially aligned, both of which extend radially inward from the outer surface 30 of the distal end region of the catheter 112.

Additionally, the detailed view of FIG. 7 illustrates the distal end 140 of the fiber optic 126 aligned with the proximal membrane 135 of the fluid lumen 122. It can be appreciated that, in some examples, the fiber optic 126 may be designed to emit a light signal 144 from its distal end 140. For example, the controller 118 may include a laser and/or LED light source which may transmit a light signal 144 through the fiber optic 126, whereby the light signal 144 passes out the distal end 140 of the fiber optic 126 toward the proximal membrane 135 of the fluid channel 122. As will be described in greater detail below, the light signal 144 passing out of the distal end 140 of the fiber optic 126 may hit the proximal membrane 135 and reflect back toward the distal end 140 of the fiber optic 126. The reflected light is illustrated by the dashed arrow 146.

In some instances, the controller 118 may include a light sensor (e.g., a photodiode) which may be designed to measure changes in the light signal 144 which is reflected back toward the fiber optic 126 (e.g., the reflected light 146 may pass through the fiber optic 126 to a photodiode in the controller 118). Additionally, it can be appreciated that because light signal 144 is aligned with the proximal membrane 135, the "pattern" of the reflected light 146 from the proximal membrane 135 may change coincident with changes in the proximal membrane 135. The changes in the light pattern reflected back from the proximal membrane 135 may be sensed by the photodiode in the controller 118.

Figure 8:
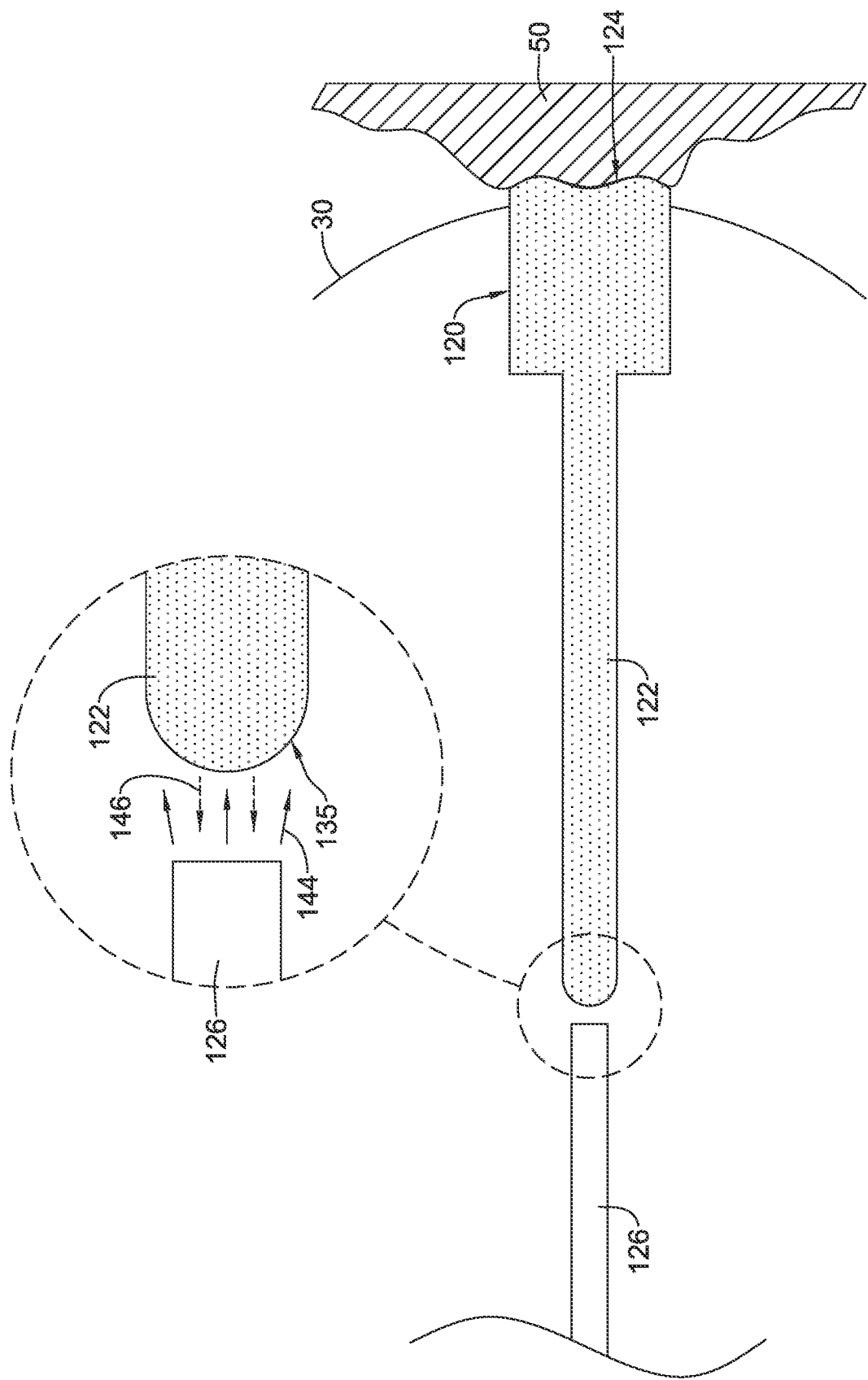
FIG. 8 is another partial cross-sectional view of an example medical device.

FIG. 7 and FIG. 8, collectively, illustrate an example in which the medical device 110 measures the pressure and/or force applied to the distal end of the medical device 110 as the medical device 110 contacts an example tissue site 50 in the body. For example, FIG. 7 illustrates the distal membrane 124 (located along the outer surface 30 of the medical device 110, as described above) near an example tissue site 50 in a patient's body. It can be appreciated from the detailed view in FIG. 7 that the proximal membrane 135 of the fluid lumen 122 has not deformed because the distal membrane 124 has not yet contacted the tissue site 50. As described above, the detailed view of FIG. 7 also illustrates the fiber optic 126 emitting a light signal 144 directed toward the proximal membrane 135 and reflected light 146 traveling back toward the fiber optic 126 from the proximal membrane 135.

FIG. 8 illustrates the position of the medical device 110 after the distal end of the medical device 110 has been advanced such that the distal membrane 124 has contacted the tissue site 50. It can be appreciated from FIG. 7 and FIG. 8 that as the distal membrane 124 contacts the tissue site 50, the distal membrane 124 may deform (e.g., the distal membrane 124 may deform as it engages the contours of the tissue site 50). Further, because the micro-fluidic cell 120 and the fluid lumen 122 are filled with an incompressible fluid, changes in shape to the distal membrane 124 may translate to changes in the proximal membrane 135. For example, the detail view of FIG. 8 illustrates the proximal membrane 135 changing shape (e.g., expanding outward) in response to changes in the distal membrane 124.

Further, as described above, changes in the shape of the proximal membrane 135 may alter the pattern of light 146 reflected back toward the fiber optic 126. Moreover, it can be appreciated that this reflected light 146 may be transmitted over the fiber optic 126 to a light sensor (e.g., photodiode) located in the controller 118. Additionally, the light sensor (e.g., photodiode) may be able to correlate the change in the pattern of reflected light 146 to varying degrees of deformity of the proximal membrane 135. In other words, as a clinician advances the medical device 110 distally, thereby imparting increasing force to the distal membrane 124, the proximal membrane 135 may increasingly deflect in response to the deflection of the distal membrane 124. These increased forces may be sensed (e.g., measured) by the photodiode located in the controller 118. Additionally, the controller 118 may be able to translate the light signals sensed by the photodiode into force (e.g., pressure) measurements corresponding to the forces imparted to the micro-fluidic cells 120 positioned on the distal end of the catheter 112.

In some examples, the fiber optic 126 described above may be described as a fiber coupler 126, whereby the fiber coupler 126 may be defined as a single fiber which may transmit light signals 144 (e.g., LED signals) from the controller 18 while also being able to transmit the reflected light signals 146 from the proximal membrane 135 to the light sensor (e.g., photodiode) in the controller 118. In other examples, however, the fiber 126 described in FIG. 7 may include two separate fibers, whereby one of the fibers transmits the light signal 144 to the proximal membrane from the controller 118 and the second fiber transmits the reflected light 146 back from the proximal membrane to the light sensor (e.g., photodiode).

Additionally, in some instances, the proximal membrane 135 may include a mirrored surface to increase the reflected light signal 146. The proximal membrane 135 may also be include a more specular or more diffuse reflection to increase or decrease its sensitivity, for example.

Further, the proximal membrane 135 may be translucent or clear. The incompressible fluid may include particles that reflect the light transmitted from the fiber optic 126. For example, the fluid may be an emulsion which can change the light signal 144 from one of surface change variability to one of volume change variability which improves the signal-to-noise ratio and/or the signal linearity characteristics.

Further yet, in some examples the diameter and area of the distal membrane 124 and/or the proximal membrane 135 may be customized in relation to one another to vary the sensitivity of light detection. Similarly, the thickness and/or elasticity of the distal membrane 124 and/or the proximal membrane 135 may be customized in relation to one another to vary the sensitivity of light detection. For example, a thinner distal membrane 124 may be more sensitive to force measurements and may be used to measure very light contact forces. Conversely, a thicker distal membrane 124 may be utilized to measure higher contact forces.

Additionally, the proximal membrane 135 itself may include a thick "skin" which changes volume in response to pressure changes of the incompressible fluid located in the fluid lumen 122. For example, the proximal membrane 135 may include a closed cell foam structure sandwiched between two membranes. As the pressure within the fluid lumen 122 rises, the closed cell foam structure may become thinner. Further, the foam may contain reflective material that reflects the incident light back to the optic fiber 126. As the foam changes thickness in relation to pressure changes, the light collected by the optic fiber 126 changes.

In another example, the proximal membrane 135 may include a compressible fluid (e.g., a gas) sandwiched between two membranes. When the pressure in the fluid lumen 122 changes, the two membranes may come closer together and change the light reflected and collected by the optic fiber 126.

In some examples, a dichroic mirror may be deposited on the distal end surface of the optic fiber 126. This may permit one wavelength of light signal be reflected back from the proximal membrane 135 and detected by a first photodiode in the controller 18. Further a second wavelength from a second light signal may be reflected directly back from the optic fiber 126 and detected by a second photodiode. The pressure signal may be calculated as the ratio between the first photodiode measurement and the second photodiode measurement. The benefit of this method is that it may reduce variability due to light losses in the optic fiber 126 due to variability in curvature and coupling.

While FIG. 7 and FIG. 8 illustrate the above pressure measurements taken by a single micro-fluidic cell 120, it can be appreciated that each individual micro-fluidic cell 120 may sense its own force measurement, thereby permitting the entire array of micro-fluidic cells 120 to transmit an array of pressure measurements to the controller 118. The controller 118 may be capable of processing the collection of pressure measurements taken from the micro-fluidic array and "map" the pressure distribution along the entire outer surface 30 of the distal end of the catheter 112.

Figure 9:
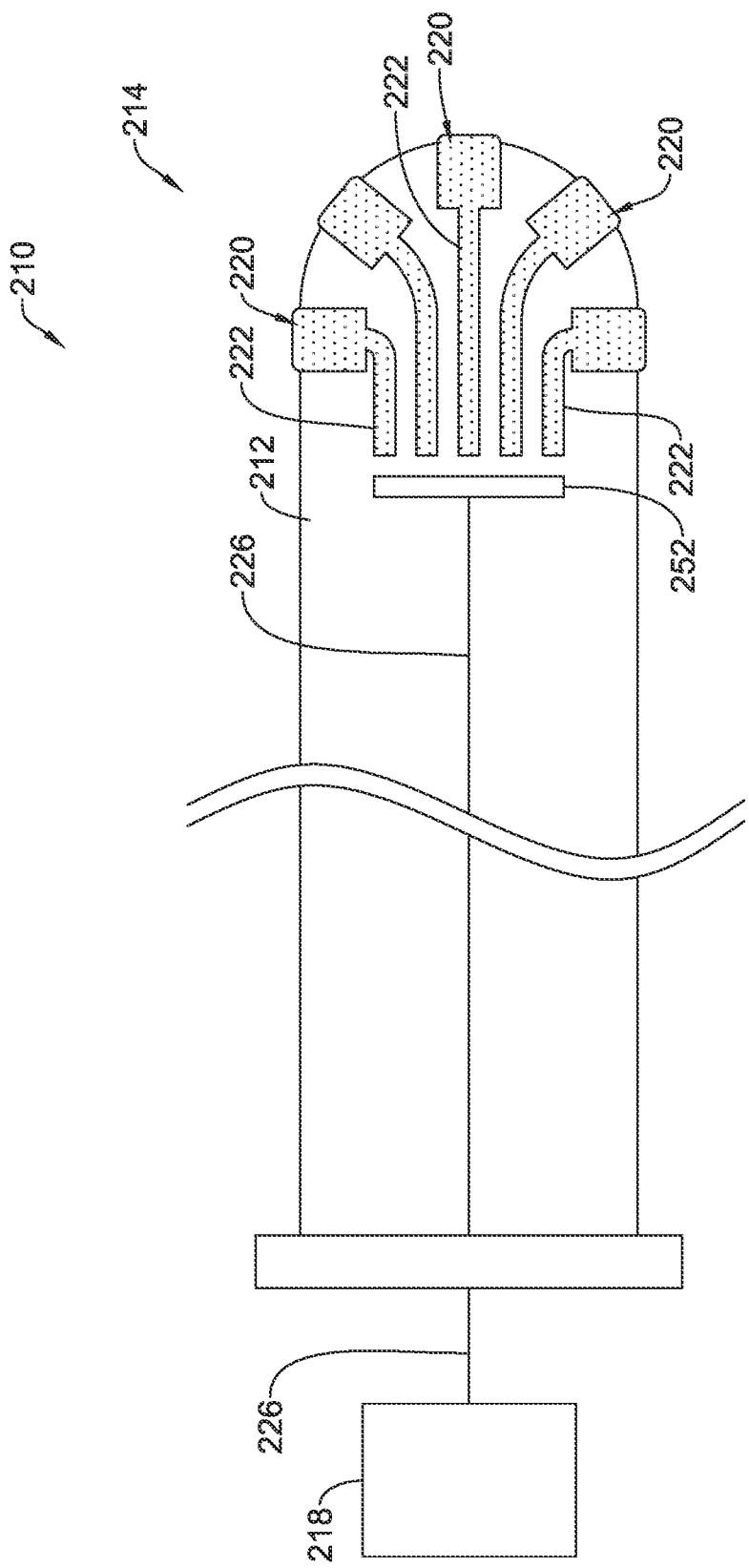
FIG. 9 is another partial cross-sectional view of an example medical device.

FIG. 9 illustrates another example medical device 210. The medical device 210 may be similar in form and function to the medical devices 10/110 described above. For example, as shown in FIG. 8, the distal end region 214 of the catheter 212 may include a plurality of micro-fluidic cells 220 (the micro-fluidic cells 220 may be similar in form and function to the fluidic cells 20/120 described above), each of which transition to a fluid lumen 222 (the fluid lumens 222 may be similar in form and function to the fluid lumens 22/122 described above). As described above with respect to medical devices 10/110, both the micro-fluidic cell 220 and the fluid lumen 222 may be filled with an incompressible fluid, whereby contact of a distal membrane located on the micro-fluidic cells 220 may be transferred via the incompressible fluid to a proximal membrane located on the fluid lumen 222.

Additionally, FIG. 9 illustrates that the medical device 210 may include a camera 252 spaced away from and aligned with all the fluid lumens 222. Additionally, an electrical cable 226 may extend proximally within the catheter 212, whereby the distal end of the electrical cable 226 may be coupled to the camera and the proximal end of the electrical cable 226 may be coupled to a controller 218 (the controller 218 may be similar in form and function to the controllers 18/118 described above).

As described above with respect to the medical devices 10/110, it can be appreciated that while a portion of the catheter 212 is positioned inside a patient's body, the controller 218 may be positioned outside the patient's body.

As described above, changes in the fluid pressure within the micro-fluidic cell 220 and the fluid lumen 222 may causes changes in the proximal membrane of the fluid lumen 222. It can further be appreciated that the physical deformation of each proximal membrane (for each of the discrete fluid lumens 222) may be sensed and measured by the camera 252. Additionally, the physical changes sensed and measured by the camera 252 may be transmitted from the camera 252 to the controller 218. This collection of signals generated and transmitted by the camera 252 may correspond to the entire array of pressure measurements taken from the micro-fluidic cells 220. Further, the controller 218 may be capable of processing the collection of pressure measurements taken from the micro-fluidic array and thereby "map" the pressure distribution along the entire outer surface 30 of the distal end of the catheter 212.

Figure 10:
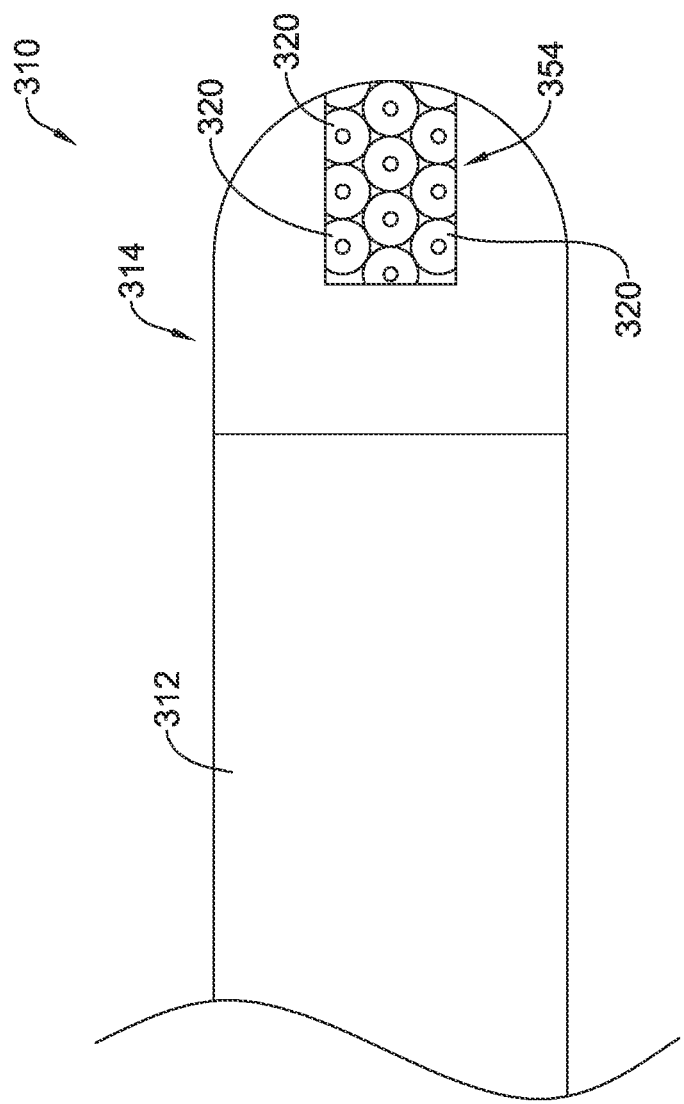
FIG. 10 is a side view of another example medical device.

FIG. 10 illustrates another example medical device 310. The example medical device 310 may be similar in form and function to the medical device 10 described above. For example, the medical device 310 may include an array 354 of micro-fluidic cells 320 disposed along a portion of the distal end region 314 of the catheter 312. However, as shown in FIG. 10, the array of micro-fluidic cells 320 may be confined to only a specific area of the distal end region 314 of the catheter 312. For example, FIG. 10 illustrates the micro-fluidic cells confined to a rectangular "strip" along the distal end region 314. However, this is not intended to be limiting. Rather, it is contemplated that the array of micro-fluidic cells may be organized in a variety of arrangements along the distal end region 314 of the catheter 312.

As discussed above, medical devices described herein may be utilized to generate an array of signal outputs from a collection of pressure elements (e.g., micro-fluidic cells). It can be appreciated that, in some instances, the medical devices utilized herein may be previously calibrated (e.g., calibrated in a laboratory outside prior to being used in a medical procedure) such that pressure signals acquired in vivo may be characterized according to a variety of different structures for which the distal end of the catheters may come into contact. For example, prior calibration may permit the medical devices to differentiate between soft and elastic body structures, or between hard and inelastic body structures, or gel-like structures, liquids, or the like.

Additionally, the pressure sensing arrays described herein may, in some examples, be used for sonic or ultrasonic wave detection.

It should be noted that the features of any of the catheters described with respect to particular figures and/or embodiments are not limited to that particular example. Rather, it is contemplated that any of the features or examples disclosed with respect to a single example may be incorporated into any other example disclosed herein.

The materials that can be used for the various components of guidewire 10 (and/or other guidewires disclosed herein) and the various devices disclosed herein may include those commonly associated with medical devices. For simplicity purposes, to the extent the following discussion makes reference to guidewire 10, it is not intended to limit the devices and methods described herein only to guidewire 10, as the discussion may be applied to other similar devices disclosed herein.

Medical device 10, components of medical device 10 and/or other medical devices (and components thereof) disclosed herein may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKmarletxELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10, components of medical device 10 and/or other medical devices (and components thereof) disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10, components of medical device 10 and/or other medical devices (and components thereof) disclosed herein in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10, components of medical device 10 and/or other medical devices (and components thereof) disclosed herein to achieve the same result.

In some embodiments, a degree of Magnetic Resonance Imaging (MRI) compatibility is imparted into the medical device 10, components of medical device 10 and/or other medical devices (and components thereof) disclosed herein. For example, the medical device 10, components of medical device 10 and/or other medical devices (and components thereof) disclosed herein, or portions thereof, may be made of a material that does not substantially distort the image and create substantial artifacts (e.g., gaps in the image). Certain ferromagnetic materials, for example, may not be suitable because they may create artifacts in an MRI image. The medical device 10, components of medical device 10 and/or other medical devices (and components thereof) disclosed herein may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
   a catheter having a proximal end region and a distal tip;
   an array of sealed chambers disposed along the distal tip, wherein each of the chambers includes a distal membrane disposed along an outer surface of the distal tip and a proximal membrane extending radially inward from the outer surface; and
   a plurality of fibers, wherein each fiber has a proximal end and a distal end, wherein the distal end of each fiber is coupled to a pressure sensor aligned with a single proximal membrane, and wherein each pressure sensor is coupled to its corresponding proximal membrane, and wherein each pressure sensor is positioned between the distal end of a fiber and its corresponding proximal membrane, and wherein at least one pressure sensor faces distally toward the distal tip of the catheter;
   wherein each proximal membrane is configured to shift between a first position and an expanded position in response to a change in pressure within the chamber;
   wherein each of the array of sealed chambers is filled with an emulsion;
   wherein the emulsion includes a plurality of light reflective particles disposed within an incompressible fluid.

2. The medical device of claim 1, wherein each sensor is configured to measure the extent to which proximal membrane shifts between the first position and the expanded position.

3. The medical device of claim 1, wherein the extent to which each of the proximal membranes expands directly corresponds to the extent of pressure change within the respective chamber to which the membrane is connected.

4. The medical device of claim 1, wherein each of the proximal membranes shifts from the first position to the expanded positioned in response to a deflection of its corresponding distal membrane.

5. The medical device of claim 1, wherein each pressure sensor is designed to transmit a pressure signal along its corresponding fiber, and wherein the pressure signal corresponds to the pressure change in the chamber to which the sensor corresponds.

6. The medical device of claim 1, wherein each of the sealed chambers includes a first cavity in fluid communication with a second cavity, wherein the first cavity includes a first diameter and wherein the second cavity includes a second diameter different from the first diameter.

7. A medical device, comprising:
a catheter having a proximal end region and a distal tip;
an array of sealed chambers disposed along the distal tip, wherein each of the chambers includes a distal membrane disposed along an outer surface of the distal tip and a proximal membrane extending radially inward from the outer surface, wherein each proximal membrane is configured to shift between a first position and an expanded position in response to a change in pressure within the chamber; and
a plurality of fibers, wherein each fiber has a proximal end and a distal end, wherein the distal end of each fiber is coupled to a pressure sensor aligned with a single proximal membrane, and wherein each pressure sensor is coupled to its corresponding proximal membrane, and wherein at least one pressure sensor faces distally toward the distal tip of the catheter;
wherein each of the fibers of the plurality of fibers includes an optical fiber;
wherein each of the array of sealed chambers is filled with an emulsion;
wherein the emulsion includes a plurality of light reflective particles disposed within an incompressible fluid.

8. The medical device of claim 7, wherein the distal end of each of the plurality of optical fibers is spaced away from the proximal membrane, and wherein each of the plurality of optical fibers is configured to transmit a first light signal onto the proximal membrane.

9. The medical device of claim 8, wherein each of the first light signals transmitted onto its corresponding proximal membrane is reflected back to each respective optical fiber, and wherein the reflected light signals correspond to the shifting of each of the respective proximal membranes.

10. The medical device of claim 9, wherein comparing the first light signal with the reflected light signal directly corresponds to a change in pressure of the chamber.

11. A medical device system, comprising:
a processor;
a catheter having a proximal end region and a distal tip, the proximal end region coupled to the processor;
a plurality of fluid sealed chambers disposed along the distal tip, wherein each of the chambers includes a distal membrane disposed along an outer surface of the distal tip and a proximal membrane extending radially inward from the outer surface;
a plurality of fibers, wherein each fiber has a proximal end and a distal end, wherein each distal end is aligned with a discrete proximal membrane; and
a plurality of pressure sensors, wherein each pressure sensor is aligned with a discrete fiber and a discrete proximal membrane, and wherein each pressure sensor is positioned between the fiber and proximal membrane with which it is aligned, and wherein at least one pressure sensor faces distally toward the distal tip of the catheter;
wherein each proximal membrane is configured to shift between a first position and an expanded position in response to a change in pressure within the chamber;
wherein each of the plurality of fluid sealed chambers is filled with an emulsion;
wherein the emulsion includes a plurality of light reflective particles disposed within an incompressible fluid.

12. The system of claim 11, wherein each sensor is configured to measure the extent to which each proximal membrane shifts between the first position and the expanded position, and wherein the sensor converts the extent to which each proximal membrane shifts between the first position and the expanded position into a pressure signal.

13. The system of claim 12, wherein each sensor is designed to transmit the pressure signal to the processor.

14. The system of claim 13, wherein the processor is configured to output an array of pressure signals corresponding to the change in pressure of each of the chambers.

15. A method for measuring pressure within a body cavity, the method comprising:
advancing a pressure catheter to a tissue site within the body cavity, the pressure catheter including:
a catheter having a proximal end region and a distal tip;
an array of sealed chambers disposed along the distal tip, wherein each of the chambers includes a distal membrane disposed along an outer surface of the distal tip and a proximal membrane extending radially inward from the outer surface, wherein each of the array of sealed chambers is filled with an emulsion, and wherein the emulsion includes a plurality of light reflective particles disposed within an incompressible fluid; and
a plurality of fibers, wherein each fiber has a proximal end and a distal end, wherein the distal end of each fiber is coupled to a pressure sensor aligned with a single proximal membrane, and wherein each pressure sensor is coupled to its corresponding proximal membrane, and wherein each pressure sensor is positioned between the distal end of a fiber and its corresponding proximal membrane, and wherein at least one pressure sensor faces distally toward the distal tip of the catheter;
engaging one or more of the distal membranes with the tissue site;
deflecting one or more proximal membranes in response to the engagement of the distal membrane with the tissue site;
measuring the deflection of the one or more proximal membranes, wherein the deflection of each of the one or more proximal membranes corresponds to the change in pressure within its respective chamber.

* * * * *